United States Patent [19]

Kimura et al.

[11] Patent Number: 4,569,343
[45] Date of Patent: Feb. 11, 1986

[54] SKIN APPLICATION MEDICAMENT

[75] Inventors: Hideo Kimura; Masahiro Tabuchi; Motokazu Iwasaki, all of Sohwa, Japan

[73] Assignee: Firma Carl Freudenberg, Weinheim, Fed. Rep. of Germany

[21] Appl. No.: 529,557

[22] Filed: Sep. 6, 1983

[30] Foreign Application Priority Data

Sep. 30, 1982 [JP] Japan ................ 57-172930

[51] Int. Cl.⁴ .................. A61F 13/00; B32B 27/00
[52] U.S. Cl. .................................. 128/155; 421/28;
428/284; 428/287; 428/288; 428/289; 428/290;
428/300; 428/297; 428/298; 428/301; 428/325;
428/397; 604/304; 604/897
[58] Field of Search .................. 128/155; 424/28;
428/284, 287, 288, 289, 290, 300, 301, 297, 298,
325, 397; 604/304, 897

[56] References Cited

U.S. PATENT DOCUMENTS

| 3,658,984 | 1/1967 | Kamp | 424/28 |
| 4,191,743 | 3/1980 | Klemm et al. | 424/28 |
| 4,211,807 | 7/1980 | Yazawa et al. | 428/290 |
| 4,486,488 | 12/1984 | Pietsch et al. | 424/28 |

Primary Examiner—John Kight
Assistant Examiner—Kriellion Morgan
Attorney, Agent, or Firm—Felfe & Lynch

[57] ABSTRACT

A skin application medicament comprising a nonwoven fabric base coated on a side thereof with a medicament and having a layer with a planar direction, the layer containing at least 20% by weight of flat fibers, the fibers each having a major axis and a minor axis and an aspect ratio of 2:1 or more and wherein in a section of said layer, as cut in the direction of thickness, the average angle between the major axis of the fibers and the layer planar direction is not more than 75°.

9 Claims, 1 Drawing Figure

U.S. Patent Feb. 11, 1986 4,569,343
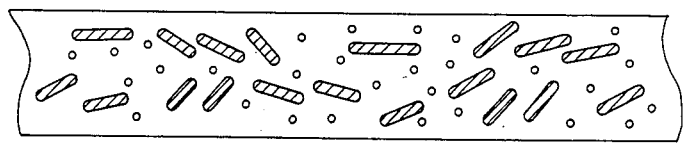

SKIN APPLICATION MEDICAMENT

BACKGROUND OF THE INVENTION

Recently, nonwoven fabrics have come to be used as a base for a compress in place of cotton flannel. Nonwoven fabrics are lower in price than cotton flannel and have good flexibility, and therefore, are suitable for use as such a base. Since they have comparatively high air permeability, however, nonwoven fabrics present a problem in that the medicament applied is apt to bleed through the back of the base. One approach considered to overcome this difficulty is to increase the weight per unit area of the nonwoven fabric. Naturally, however, this approach will involve higher price and lower flexibility, thus diminishing the advantages of the nonwoven fabric.

Bleeding of the medicament is attributable to the presence of openings formed by and among the component fibers of the nonwoven fabric. Moreover, nonwoven fabrics presently used have a substantial number of large openings per unit area.

SUMMARY OF INVENTION

After an extensive study, the present inventors have found that it is possible to block off such openings by using a special type of fiber as component fiber to prevent the bleeding of medicament.

The present invention relates to a skin application medicament comprising a medicament coated on one side of a base. More specifically, the invention relates to a compress having such medicament as kaolin clay, glycerine, methyl salicylate, or l-menthol coated on one side of the base.

The medicament is coated on one side of a nonwoven fabric base, wherein said base has a layer containing at least 20 wt % of flat fibers, each having an aspect ratio (major-axis to minor-axis ratio) of 2:1 or more wherein the average angle between the major-axis direction of the individual fibers and the plane direction of said layer is not more than 75° in a section of said layer as cut in the direction of thickness.

The various features of novelty which characterize the invention are pointed out with particularity in the claims annexed to and forming a part of this specification. For a better understanding of the invention, its operating advantages and specific objects obtained by its use, reference should be had to the accompanying drawing and descriptive matter in which there is illustrated and described a preferred embodiment of the invention.

BRIEF DESCRIPTION OF THE DRAWING

The single FIGURE is a schematic view showing an electron-microscopic observation of a section of a layer containing flat fibers, as cut in the direction of thickness.

DESCRIPTION OF PREFERRED EMBODIMENT

The present invention is in a skin application medicament wherein the medicament is coated on one side of a nonwoven fabric base, the base having a layer containing at least 20% by weight of flat fibers having an aspect ratio of at least 2:1 and wherein the average angle between the orientation of the individual fibers major axis and the plane direction of the layer is not more than 75°.

The flat fibers used in the present invention refer mainly to those having an ellipsoidal or quadrangular cross section. The term "flat fiber" also embraces those having a "<" or "C" shaped cross section. Normally, the component fibers of a nonwoven fabric have a circular cross section. In contrast with such fibers, flat fibers are advantageous in that they can block off openings formed by and among the component fibers of a nonwoven fabric when used therein.

The flat fibers employed in the invention must have an aspect ratio of 2:1 or more. By the term "aspect ratio" used herein is meant the ratio of the major axis to the minor axis in the cross sectional configuration of the fiber. If the cross section is ellipsoidal, the aspect ratio refers to the ratio between the major axis and the minor axis in the ellipsoid. In the case of quadrangular cross section, it refers to the ratio between the major and minor sides. If the cross section is of "<" or "C" configuration, a straight line connecting between the left end and the right end is taken as the major axis and the thickness of the fiber is taken as the minor axis. If the aspect ratio is less than 2:1, the cross section is close to a circular configuration and the fiber is less able to block off interfiber openings; so, such fiber is unsuitable for the purpose of the present invention. The flat fiber may be of any fineness, but in order that interfiber openings may be blocked off without sacrificing the flexibility of the base, the fiber is preferably of about 10 denier or below.

The flat fibers contained in said layer should be in a proportion of not less than 20 wt %. If the nonwoven fabric consists, for example, of two fiber-assembly layers of different compositions (in which case the fabric is called a two-layer nonwoven fabric), said layer is one of those layers. This also applies in the case of nonwoven fabrics having three or more layers. If the nonwoven fabric is of a single composition, the entire fabric is called a layer. If the flat fiber content of such layer is less than 20 wt %, the blocking off of fiber openings is insufficient and therefore such layer is unsuitable for the purpose of this invention. The fibers other than flat fibers employed in the invention may be any natural fiber, semi-synthetic fiber, or synthetic fiber having a substantially circular cross section. The flat fiber and other fibers employed may be of such known compositions as polypropylene, polyethylene, polyamide, polyester, or cellulose.

The sectional configuration of a flat-fiber containing layer as cut in the direction of thickness is as shown in the drawing. Those appearing quadrangular represent flat fibers and those appearing round shaped represent other fibers contained in the layer. The quadrangular ones are seen in varying sizes because they are not necessarily cut right along the section, with some cut at oblique angles.

In the present invention, the average angle between the major-axis direction of the individual flat fibers and the planar direction of the said layer should be not more than 75°. The major-axis direction referred to herein normally corresponds to the longitudinal axis of cross section of the flat fiber. However, if the aspect ratio of the flat fiber is so great that the major axis is folded, a straight line connecting between the left and right ends of the major axis is taken as the major-axis direction. The term "planar direction" refers to the planar surface of the layer, that is, a plane perpendicular to the thicknesswise direction. In the invention it is important that the average angle between the major-axis directions and the planar direction should be not more than 75°. If the average angle is greater than 75° and close to 90°, the major-axis directions of the flat fibers are substantially in the thickness direction. This will reduce the effect of the flat fibers blocking off the interfiber openings which cause bleeding of medicament coated on one side of the nonwoven fabric base. The average angle of not greater than 75° is a value obtained by dividing the sum of measurements as to angles of the major-axis directions to the planar direction in a given section (that is, angle in the acute-angled portion) by the number of measurements. More specifically, about five specimens in each of which sections of 10 to 20 flat fiber ends can be observed are taken to be measured by electron-microscopic observation or otherwise as to the angle between the major-axis direction of each flat fiber and the planar direction of the layer; and the average value of the measurements is taken as average angle.

A layer containing flat fibers arranged in such a specific way may be obtained by incorporating flat fibers into a fiber sheet in a carding process. Alternatively, the layer can be obtained by lightly pressing flat fibers after they are carded and assembled. The layer may be subjected to needling as required in order to improve its mechanical strength. This may tend to orient the flat fibers in the direction of thickness, but it is acceptable unless the direction of the major axis tends to coincide with the thickness direction.

A nonwoven fabric base having such a layer is coated on one side thereof with any desired medicament. Since the flat fibers are present in flat laid condition within the layer, the interfiber openings are effectively blocked off and thus the medicament is prevented from bleeding through the base to the back thereof.

The skin application medicament can be used not only as a compress, but also for various external applications such as plaster, adrenocortical hormone liniment, and hemorrhoids treatment.

The invention is illustrated by the following examples:

EXAMPLE 1

Fifty weight percent of 5 denier flat rayon fiber having an aspect ratio of 20:1 was mixed with 50 wt. % of a side-by-side type composite fiber (of 3 denier and having a circular section) consisting of polyethylene component and polypropylene component, and the mixture was opened by a carding process and formed into a sheet-form web. The web was heat treated at 140° C. under pressure for 30 seconds whereby the polyethylene component of the composite fiber was softened and melted to cause the component fibers to be interconnected. The nonwoven fabric thus obtained was 60 g/m² in weight and 0.50 mm in thickness. One side of the nonwoven fabric, which was employed as the base, was coated with a soft external-application medicament including kaolin clay (45 parts by weight), refined water (30 parts by weight), glycerin (20 parts by weight) and polyvinylalcohol (10 parts by weight) as principal ingredients and, in addition, small amounts of methyl salicylate, peppermint oil, l-menthol, and diphenhydramine hydrochloride. A releasable film was placed on the external application medicament. A skin application medicament in accordance with the invention was thus obtained.

COMPARISON EXAMPLES

For evaluation purposes with respect to the product of the invention, the following three reference products were prepared.

(1) Reference product A

Fifty weight percent of 3-denier rayon fiber having a circular section was mixed with 50 wt. % of the same composite fiber as used in Example 1, and the mixture was made into a base in the same manner as described in Example 1. The same external application medicament of soft type as used in Example 1 was coated on the base and a skin application medicament was thus obtained. The nonwoven fabric was 60 g/m² in weight and 0.63 mm in thickness.

(2) Reference product B

Same as Reference product A except that the weight and thickness were different, which were 90 g/m² and 0.85 mm respectively.

(3) Reference product C

On the surface of the base, corresponding to the coating surface for soft-type external application medicament in Reference product A, was coated as a sealer a composition consisting of kaolin clay (80 parts by weight), polyvinylalcohol (10 parts by weight) and polyacrylic ester (10 parts by weight), in the amount of 40 g/m². The same soft medicament as used in Example 1 was coated on the base.

EVALUATION

After being wrapped in the conventional way, the product of the invention and reference products A, B and C were placed under a load of 1 kg/10 cm×15 cm at 40° C., and changes with time were observed as to bleeding of the soft medicament through the base to the outer surface thereof. Observation was made with 5 pieces of each product. The results are as shown in the following table.

|  | 5 days | 10 days | 15 days | 20 days |
| --- | --- | --- | --- | --- |
| Product of the invention | − | − | − | − |
| Reference product A | + | ++ | ++ | ++ |
| Reference product B | − | − | ± | + |
| Reference product C | − | − | − | ± |

− With all of the five, no bleeding at all.
± Slight bleeding was observed with some of the five.
+ Bleeding was observed with all of the five.
++ Bleeding in excess of 20% of the total area was observed with all of the five.

EXAMPLE 2

Fifty weight percent of 1.5 denier flat nylon fiber having an aspect ratio of 2.5:1 was mixed with 30 wt % of 3-denier polyester fiber having a circular section and 20 wt % of 3-denier rayon fiber having a circular section, and the mixture was opened by a carding process and formed into a sheet-form web having a weight of 40 gm/m². Polyacrylic ester in the form of an emulsion, as an interfiber binder, was impregnated into the web, and then dried. Thus, a nonwoven fabric of 60 g/m² in weight was obtained. Using the fabric as the base, the same soft medicament as used in Example 1 was coated on the base and a skin application medicament was obtained. Five specimens of the product were subjected to an evaluation test in the same manner as Example 1, and no bleeding was observed with all of the five specimens 20 days after the start of the test.

EXAMPLE 3

Sixty weight percent of 5-denier flat rayon fiber having an aspect ratio of 20:1 and 40 wt % of 3-denier polyester fiber having a circular section were mixed together, and the mixture was opened and formed by a carding process into a web having a weight of 12 g/m². A polyacrylic ester emulsion, as an interfiber bonding agent, was impregnated into the web, and subsequently the web was dried. Thus a nonwoven fleece of 15 g/m² was obtained. Over this fleece a web, consisting of 3-denier polyester fiber having a circular section, said web having a weight of 85 g/m², was laminated. The laminate was subjected to needle punch. The nonwoven fabric thus obtained had a two-layer structure, one layer containing flat fibers and the other layer containing no flat fiber. Subsequently, the nonwoven fabric was coated on the flat fiber containing fleece side with the same soft medicament as used in Example 1. The skin application medicament was evaluated in the same manner as in Example 1. No bleeding was observed with all of the five specimens 4 weeks after the start of the test.

COMPARISON EXAMPLE

By using a 5-denier rayon fiber having a circular section in place of the flat fiber used in Example 3, a nonwoven fabric having a two-layer structure similar to the one in Example 3 was obtained. The nonwoven fabric so obtained was coated with a soft medicament. The resulting skin application medicament was evauated in the same as in Example 1. Bleeding was observed with all of the five specimens two weeks after the start of the test.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A skin application medicament comprising a nonwoven fabric base coated on a side thereof with a medicament and having a layer with a planar direction, the layer containing at least 20% by weight of flat fibers, the fibers each having a major axis and a minor axis and an aspect ratio of 2:1 or more and wherein in a section of said layer, as cut in the direction of thickness, the average angle between the major axis of the fibers and the layer planar direction is not more than 75°.

2. The skin application medicament of claim 1, wherein the fiber is 10 denier or below.

3. The skin application medicament of claim 1, wherein the nonwoven fabric is a two-layer construction.

4. The skin application medicament of claim 1, wherein the nonwoven fabric is a three-layer construction.

5. The skin application medicament of claim 1, wherein the fibers are polypropylene, polyethylene, polyamide, polyester, cellulose or mixtures thereof.

6. The skin application medicament of claim 1, wherein the coated medicament includes kaolin clay, glycerin, water and polyvinylalcohol.

7. The skin application medicament of claim 1, wherein the fiber has an ellipsoidal cross section.

8. The skin application medicament of claim 1, wherein the fiber has a quadrangular cross section.

9. The skin application medicament of claim 1, wherein the fiber has a "<" or "C" cross section.

* * * * *